United States Patent
Hartley et al.

(10) Patent No.: US 7,998,187 B2
(45) Date of Patent: *Aug. 16, 2011

(54) STENT GRAFT CONNECTION ARRANGEMENT

(75) Inventors: David Ernest Hartley, Subiaco (AU); Eric L. G. Verhoeven, Glinnen (NL)

(73) Assignees: William A. Cook Australia Pty. Ltd., Queensland (AU); Cook Medical Technologies LLC, Bloomington, IN (US)

( * ) Notice: Subject to any disclaimer, the term of this patent is extended or adjusted under 35 U.S.C. 154(b) by 129 days.

This patent is subject to a terminal disclaimer.

(21) Appl. No.: 11/231,458

(22) Filed: Sep. 21, 2005

(65) Prior Publication Data

US 2006/0095114 A1    May 4, 2006

Related U.S. Application Data

(60) Provisional application No. 60/611,610, filed on Sep. 21, 2004.

(51) Int. Cl.
*A61F 2/06* (2006.01)

(52) U.S. Cl. .................... 623/1.13; 623/1.16; 623/1.18; 623/1.35

(58) Field of Classification Search ........ 623/1.13–1.26, 623/1.35, 1.36, 2.1, 2.14, 2.18, 2.16, 1.3–1.32; 285/231–236; 24/26–29; 604/533–536, 604/539; 606/108, 194, 198, 153
See application file for complete search history.

(56) References Cited

U.S. PATENT DOCUMENTS

| | | | | |
|---|---|---|---|---|
| 4,907,336 | A * | 3/1990 | Gianturco | 29/515 |
| 5,609,627 | A * | 3/1997 | Goicoechea et al. | 128/898 |
| 5,824,037 | A * | 10/1998 | Fogarty et al. | 623/1.13 |
| 5,824,040 | A * | 10/1998 | Cox et al. | 623/1.35 |
| 5,993,481 | A * | 11/1999 | Marcade et al. | 623/1.35 |
| 6,099,558 | A * | 8/2000 | White et al. | 623/1.16 |
| 6,221,102 | B1 * | 4/2001 | Baker et al. | 623/1.36 |
| 6,287,330 | B1 * | 9/2001 | Johansson et al. | 623/1.13 |
| 6,322,587 | B1 * | 11/2001 | Quiachon et al. | 623/1.23 |
| 6,355,061 | B1 * | 3/2002 | Quiachon et al. | 623/1.36 |
| 6,375,675 | B2 * | 4/2002 | Dehdashtian et al. | 623/1.13 |
| 6,416,542 | B1 * | 7/2002 | Marcade et al. | 623/1.16 |
| 6,451,053 | B1 * | 9/2002 | Dehdashtian et al. | 623/1.34 |
| 7,112,217 | B1 * | 9/2006 | Kugler et al. | 623/1.31 |
| 2001/0010015 | A1 * | 7/2001 | Hijlkema | 623/1.16 |
| 2003/0135261 | A1 * | 7/2003 | Kugler et al. | 623/1.13 |
| 2003/0139797 | A1 * | 7/2003 | Johnson et al. | 623/1.13 |
| 2003/0199967 | A1 * | 10/2003 | Hartley et al. | 623/1.13 |
| 2006/0136031 | A1 * | 6/2006 | Gallo et al. | 623/1.11 |

* cited by examiner

*Primary Examiner* — Elizabeth Houston
(74) *Attorney, Agent, or Firm* — Richard J. Godlewski

(57) ABSTRACT

A connection socket (12) for an end of a stent graft or a side arm (10) of a stent graft. The connection socket has a first resilient ring (14) around the arm at its end, a second resilient ring (16) spaced apart along the arm from the first ring and optionally a zig zag resilient stent (20) between the first and second rings. Each of the rings is of slightly lesser diameter than the side arm. The zig-zag resilient stent can be a compression stent.

6 Claims, 4 Drawing Sheets

STENT GRAFT CONNECTION ARRANGEMENT

CROSS-REFERENCE TO RELATED APPLICATIONS

This application claims priority of provisional application Ser. No. 60/611,610, filed Sep. 21, 2004.

TECHNICAL FIELD

This invention relates to a stent graft used to restore the patency of a body lumen and in particular relates to a connection arrangement on such a stent graft.

BACKGROUND OF THE INVENTION

Where damage has occurred to an internal vessel of the human or animal body such as to a blood vessel either by disease or by trauma, it is possible to introduce to the blood vessel a stent graft by endoluminal techniques which will restore patency of the blood vessel across the damaged region. Often such damaged regions include branch vessels. To ensure the blood flow can go into the branch vessel, bifurcated or side branch stent grafts are used.

There can be a problem with such bifurcated or side branch stent grafts in that to provide a connection into a branch vessel from a stent graft through the bifurcation or side arm a connection arrangement is needed. There have previously been proposed socket type connections in which connection is achieved by overlap of an inner and outer tube, however, owing to movement of a stent graft due to migration or change in physiology such overlap connections can become dislodged.

A similar problem exists with side arm stent grafts in that once a side arm stent graft is deployed in place and a bridging stent graft or stent is be deployed to extend from the side arm into a branch vessel there can be a problem with successful retention of such a bridging stent into the side arm.

It is an object of this invention to provide solutions to these problems or to at least provide a practitioner with an alternative a branch connector system.

Throughout this specification the term distal when used with respect to a portion of the vasculature, a deployment device or a prosthesis is the end of the vasculature, deployment device or prosthesis further away in the direction of blood flow away from the heart and the term proximal means the portion of the vasculature, deployment device or end of the prosthesis nearer to the heart. When applied to other vessels similar terms such as caudal and cranial should be understood.

SUMMARY OF THE INVENTION

In one form the invention is said to reside in a connection socket for a stent graft having a tubular body of a biocompatible material, the socket comprising a first resilient ring around the tubular body at one end thereof and a second resilient ring spaced apart along the tubular body from the first ring.

Preferably the first resilient ring and the second resilient ring are of lesser diameter than the diameter of the tubular body. Preferably the connection socket further comprises a resilient stent between the first and second rings.

The resilient stent may be a zig zag resilient stent. Preferably the resilient stent is on the outside of the tubular body.

Preferably also the first and second rings are on the outside of the tubular body.

Preferably the first and second rings comprise a material selected from shape memory wire, stainless steel or plastics material. In one embodiment the first and second rings may comprise at least two turns of wire with each end terminating in a loop.

Preferably the zig zag resilient stent is comprised of a shape memory wire and the zig zag resilient stent defines a cylindrical form having a diameter less than that of the tubular body and is thus a self contracting stent, that is, when the stent is expanded beyond its rest diameter it tends to contract to return to its rest diameter.

In an alternative form the invention is said to reside in a stent graft comprising a main tube of a biocompatible graft material and a side arm being a tube of biocompatible graft material extending from the main tube and being in fluid communication therewith, a connection socket on the side arm for a bridging stent, the connection socket comprising a first resilient ring around the side arm adjacent to the distal end thereof, a second resilient ring spaced apart along the side arm from the first ring and a zig zag resilient stent between the first and second rings.

In an alternative form the invention is said to reside in a bifurcated stent graft comprising a main tube of a biocompatible graft material and a bifurcation defining first and second legs extending from the main tube and being in fluid communication with the main tube, each of the legs being formed from a tube of biocompatible graft material, a connection socket on at least one of the legs for a leg extension, the connection socket comprising a first resilient ring around the leg adjacent the distal end thereof, a second resilient ring spaced apart along the leg from the first ring and a zig zag resilient stent between the first and second rings.

The bifurcated stent graft may have a shorter and a longer leg and the connection socket may be on the shorter leg.

It will be seen that by this invention the portion of tubular graft material with the pair of rings and with a resilient stent between them there is provided an efficient sealing region into which can be deployed a self-expanding or a balloon expanded stent, either of which can be covered, and which when allowed to expand into the connection socket is in effect firmly gripped by the first and second rings and has a resilient connection with the zig-zag resilient stent between the first and second rings.

BRIEF DESCRIPTION OF THE DRAWING

This then generally describes the invention but to assist with understanding reference will now be made to the accompanying drawings which show various embodiments of the invention.

In the drawings.

DETAILED DESCRIPTION

Figure 1:
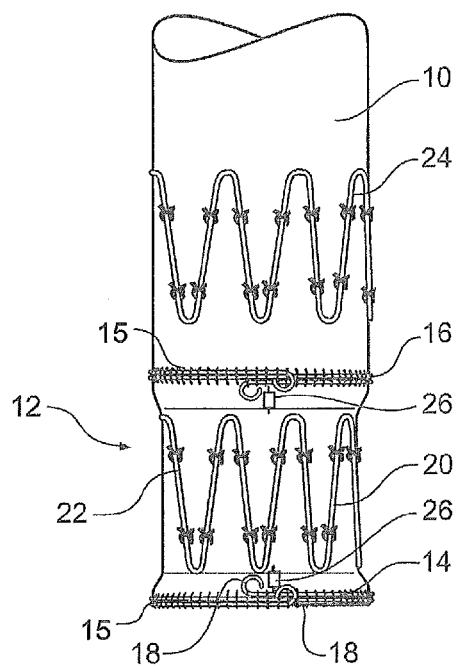
FIG. 1 shows one form of connection socket according to the present invention.
Figure 2:
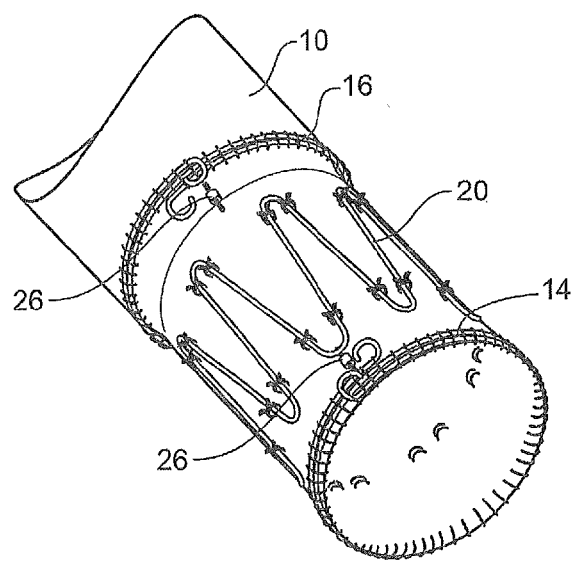
FIG. 2 shows a perspective view of the embodiment of FIG. 1.

Now looking at the drawings and more particularly the first embodiment of connection socket according to the present invention shown in FIGS. 1 and 2.

The connection socket for this embodiment of the invention may be for a side arm for a stent graft or may be for a terminal end of a leg of a bifurcated stent graft or an aorta-uni iliac stent graft adapted to be deployed into the aortic bifurcation.

In this embodiment the tube 10 may be a side arm for a stent graft or may be a terminal end of a leg of a bifurcated stent graft or of an aorta-uni iliac stent graft. The tube 10 has a socket arrangement 12 into which may be placed a self-expanding stent, a balloon expandable stent or a composite stent or leg extension. The tube 10 has a first ring 14 stitched to its terminal end and a second ring 16 spaced apart from the first ring 14. Each ring 14 and 16 is formed from at least two turns and preferably three turns of a shape memory wire such as nitinol wire and the ends of the nitinol wire terminate in loops 18. The use of the loops 18 prevent sharp ends from the nitinol wire from digging into the vasculature into which the stent graft is deployed. The rings 14 and 16 are stitched to the tube 10 by stitching 15. The rings 14 and 16 can alternatively be formed from stainless steel wire, plastics material or other suitable material. Stitching of the loops on the rings to the biocompatible graft material also prevents the resilient rings from being expanded by the pressure of a self expanding or balloon expandable stent placed therein and expanded.

Between the first ring 14 and the second ring 16 is a stent 20 formed from a resilient material. The resilient stent 20 is formed from nitinol wire, for instance, and defines a cylindrical form having a diameter less than that of the tube 10 whereby to define a self contracting stent and hence when sewn on to the outside of the tube 10 using stitching 22 it provides a diameter reducing effect on the tube 10. A further self-expanding stent 24 can be placed on the tube 10 to maintain patency of the tube.

The rings 14 and 16 provide a firm expansion restricting structure into which a balloon expandable covered or uncovered stent can be expanded or into which a stent including a self expanding stent can be deployed and the resilient stent 20 between them assists with gripping the balloon expandable covered or uncovered stent or a graft including a self expanding stent to provide a good seal.

Also provided on the tube 10 are radiopaque markers 26 adjacent each of the rings 14 and 16. These markers enable the physician to visualize the side arm and rings during an operation to assist with correct placement of a leg extension into the tube 10.

Figure 3:
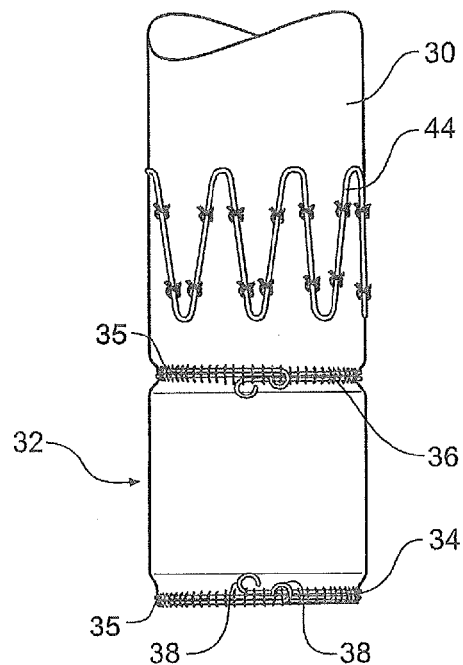
FIG. 3 shows an alternative form of connection socket according to the present invention.

FIG. 3 shows an alternative embodiment of connection socket according to the present invention. In this embodiment the tube 30 may be a side arm for a stent graft or may be a terminal end of a leg of a bifurcated stent graft or of an aorta-uni iliac stent graft. The tube 30 has a socket arrangement 32 into which may be placed a self-expanding stent, a balloon expandable stent or a composite stent or leg extension. The tube 30 has a first ring 34 stitched to its terminal end and a second ring 36 spaced apart from the first ring 34. Each ring 34 and 36 is formed from at least two turns and preferably three turns of a shape memory wire such as nitinol wire and the ends of the nitinol wire terminate in loops 38. The use of the loops 38 prevent sharp ends from the nitinol wire from digging into the vasculature into which the stent graft is deployed. The rings 34 and 36 are stitched to the tube 30 by stitching 35. The rings 34 and 36 can alternatively be formed from stainless steel wire, plastics material or other suitable material.

The rings 34 and 36 provide a firm expansion restricting structure into which a balloon expandable covered or uncovered stent can be expanded or into which a graft including a self expanding stent can be deployed.

Figure 4:
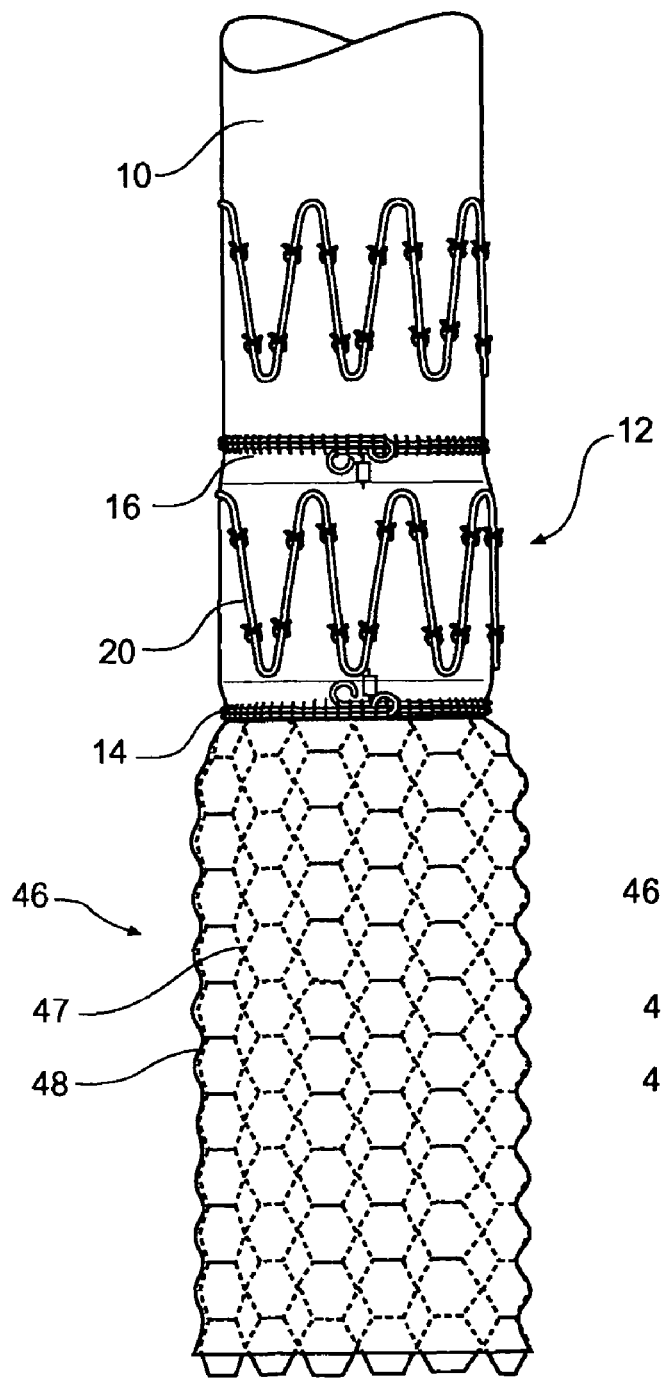
FIG. 4 shows the embodiment of FIG. 1 with a balloon expanded stent joined into the connection socket.
Figure 5:
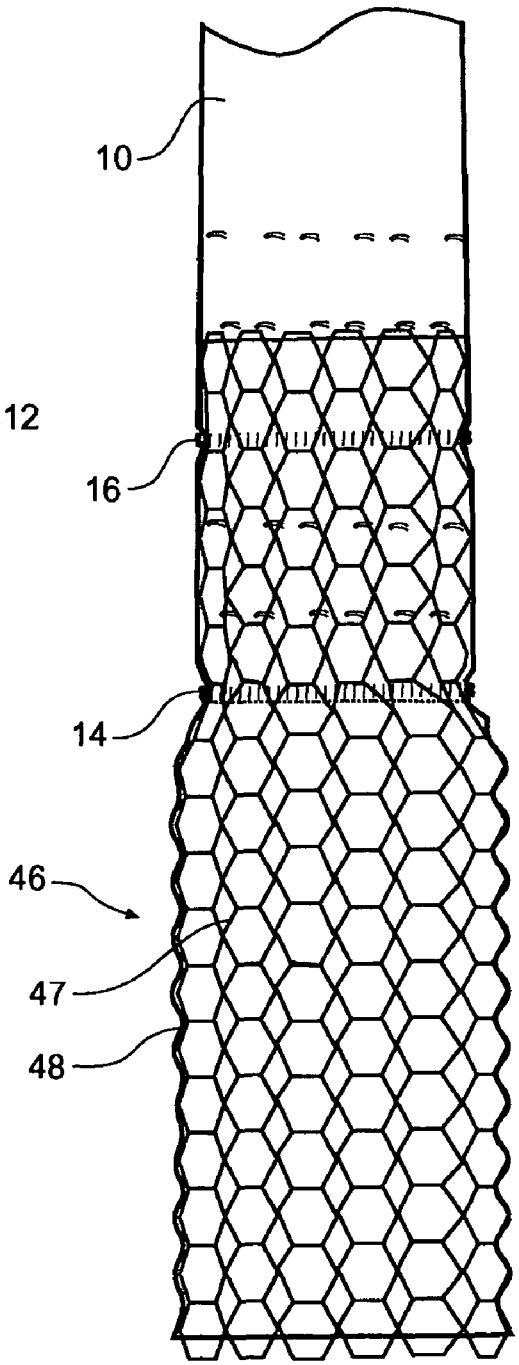
FIG. 5 shows a longitudinal cross section of the connection socket of FIG. 4.

When a balloon expandable stent or balloon expanded covered stent 46 is placed into the socket 12, of the type shown in FIG. 1, as shown in FIGS. 4 and 5 and expanded the rings 14 and 16 provide firm locking for the balloon expanded covered stent 46 and the resilient stent 20 which is expanded by the balloon expanded stent while it is being balloon expanded provides a compressive effect to keep tension on the balloon expanded stent 46. The balloon expandable covered stent 46 comprises a mesh of a shape memory metal 47 such as nitinol or stainless steel and a cover 48 of a biocompatible graft material such as woven or non-woven material selected from the group comprising Dacron and expanded PTFE or an elastomeric biocompatible material such as Thoralon®. By this means a firm connection and an improved seal can be obtained between a stent leg or arm 10 and a bridging stent 46. A similar gripping effect can be obtained with the use of a self-expanding stent, a composite stent or other form of leg extension.

Thoralon® is a polyurethane multi-polymer comprising a high flex life elastomer base with a surface modifying agent comprising siloxane which is manufactured by Thorotec Corporation (Pleasanton, Calif. USA). It will be noted from FIG. 5 that the balloon expanded covered stent 46 extends within the tube 10 to past the inner ring 16 and that the balloon expanded covered stent 46 is deformed around each of the rings to assist with locking of the balloon expanded covered stent 46 onto the tube 10. In one particular embodiment the side tube 10 may have a diameter of 8 mm and hence a circumference of 26 mm. Each of the rings may have a diameter at rest of 7 mm and the resilient stent 20 formed from nitinol wire may have a diameter at rest of 6 mm. The first and second rings 14 and 15 may be spaced apart by 10 mm and the length of the resilient stent 20 may be 6 mm. Hence there may be a gap between the rings and the resilient stent at each side of the stent of 2 mm.

Figure 6:
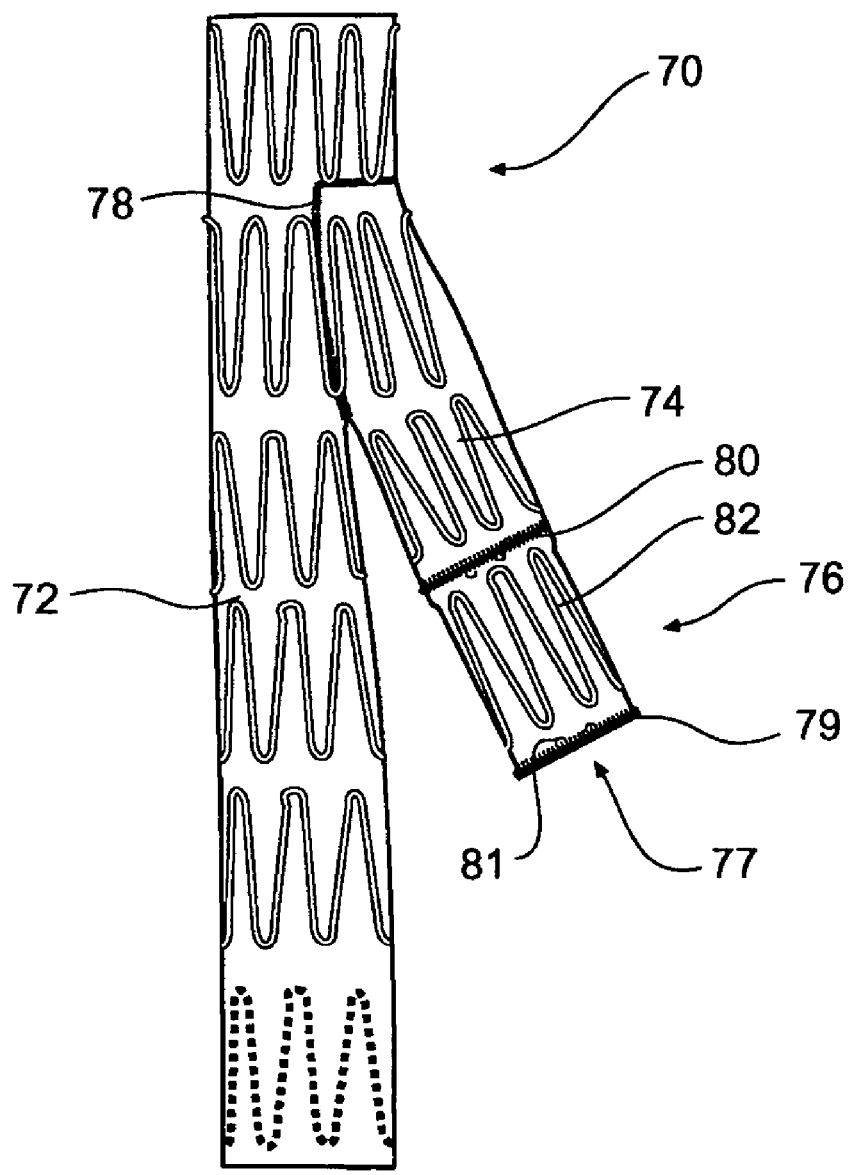
FIG. 6 shows a side branch stent graft of a type adapted for deployment into an iliac artery and including a connection socket according to one embodiment of the present invention.

In the case of a stent graft to be deployed into the common iliac artery with the side arm adapted to extend towards the internal iliac artery the side arm may have a diameter of 8 mm and a length after the join of up to 25 mm. It will be realised that for stent grafts to be deployed into the ascending or descending aorta with side arms to extend into their respective branch vessels other lengths and diameters will be applicable. FIG. 6 shows a side branch stent graft or prosthesis of the type adapted for deployment into the iliac arteries, for instance, such that a bridging stent can extend from the side arm into the internal iliac or hypogastric artery.

The stent graft 70 has a main tubular body 72 and a side arm 74. Both the main tubular body and the side arm are formed from a seamless tube of a biocompatible graft material such as Dacron. A triangular aperture is formed in the main tube and a bevel cut into the inner end of the side arm and the side arm stitched into the triangular aperture with stitching 78. The side arm has a connection socket arrangement 76 at its distal end 77. The connection socket arrangement 76 comprises a first ring 79 stitched to its terminal or distal end 77 and a second ring 80 spaced apart from the first ring 79. Each ring 79 and 80 is formed from at least two turns and preferably three turns of nitinol wire and the ends of the nitinol wire terminate in loops 81. The use of the loops 81 prevents sharp ends from the nitinol wire from digging into the vasculature into which the stent graft is deployed. Also the loops 81 enable the ends of the wires forming the rings to be stitched to the fabric of the graft which assists with preventing the rings from expanding in use. Between the first ring 79 and the second ring 80 is a stent 82 formed from a resilient material. The resilient stent 82 is formed from nitinol wire, for instance, and is made to be of a size which at rest is slightly smaller than the diameter of the side arm 74 and hence when sewn on to the outside of the side arm 74 it provides a diameter reducing effect on the side arm 74.

When a bridging stent, such as a balloon expandable stent, is placed into the socket 76 and expanded, the rings 79 and 80 provide firm locking for the balloon expanded stent and the resilient stent 82 which is expanded by the balloon expanded stent while it is being balloon expanded, provides a compressive effect to keep tension on the balloon expanded stent. By this means a firm connection and an improved seal can be obtained between the side arm and a bridging extension. A similar gripping effect can be obtained with the use of a bridging extension in the form of a self-expanding stent, a composite stent or other form of leg extension.

Figure 7:
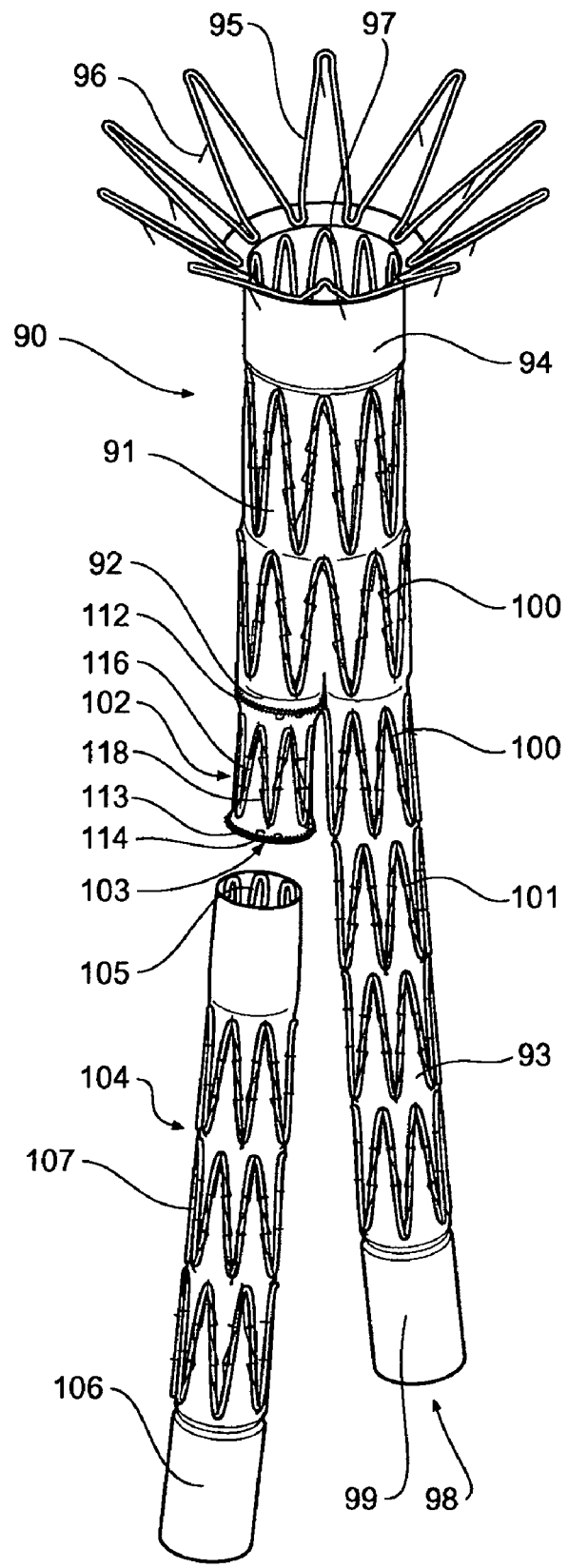
FIG. 7 shows an embodiment of a bifurcated stent graft with a connection socket according to one embodiment of the present invention.

FIG. 7 shows an embodiment of a bifurcated stent graft or prosthesis with a connection socket according to this invention. The bifurcated prosthesis 90 has a generally inverted Y-shaped configuration having a body portion 91, a shorter leg 92 and a longer leg 93. The body of the prosthesis is constructed from a tubular woven biocompatible synthetic material such as dacron. At the proximal end 94 of the prosthesis 90 is a first zigzag stent 95 which extends beyond the end of the prosthesis and has distally extending barbs 96. The prosthesis has a number of zigzag stents mounted to it and extending along its length. The stent 97 nearest the proximal end 94 is inside the tubular material so that the outside presents a smooth surface which in use engages against the inner wall of the vessel into which it is deployed to provide a barrier to the flow of blood. The stent 98 nearest the distal end 99 of the longer leg 93 is also inside the tubular material so that the outside presents a smooth surface which in use engages against the inner wall of the vessel into which it is deployed to provide a barrier to the flow of blood. Between these internal stents the rest of the stents 100 are arranged on the outside of the tubular material so that they present minimal restriction to the flow of blood through the prosthesis and present minimal sites for the growth of thromboses within the prosthesis. Each stent is sewn to the tubular material as shown particularly at 101.

The shorter leg 92 has a connection socket 102 at it distal end. The connection socket comprises a first ring 113 stitched to its terminal or distal end 103 and a second ring 112 spaced apart from the first ring 113. Each ring 113 and 112 is formed from at least two turns and preferably three turns of nitinol wire and the ends of the nitinol wire terminate in loops 114. The use of the loops 114 prevent sharp ends from the nitinol wire from digging into the vasculature into which the stent graft is deployed. Between the first ring 113 and the second ring 112 is a stent 116 formed from a resilient material. The resilient stent 116 is formed from nitinol wire, for instance, and is made to be of a size which is at rest slightly smaller than the diameter of the shorter leg 92 and hence when sewn on to the outside of the shorter leg 92 using stitching 118 it provides a diameter reducing effect on the shorter leg.

In use the prosthesis according to this embodiment of the invention is adapted for fitting into aorta such that the proximal end 94 is just distal of the renal arteries and the first zigzag stent 95 extends up to or over the renal arteries. As the stent is constructed from thin wire it does not obstruct the renal arteries if it extends over them. The longer leg 93 extends down one of the iliac arteries and the shorter leg terminates in the aorta just short of the other iliac artery at the aortic bifurcation. An extension prosthesis 104 is adapted for fitting into the connection socket 102 on the shorter leg. The extension prosthesis 104 is constructed from a tubular synthetic material such as dacron and has terminal internal stents 105 and a plurality of external intermediate stents 106.

Throughout this specification various indications have been given as to the scope of this invention but the invention is not limited to any one of these but may reside in two or more of these combined together. The examples are given for illustration only and not for limitation.

Throughout this specification and the claims that follow unless the context requires otherwise, the words 'comprise' and 'include' and variations such as 'comprising' and 'including' will be understood to imply the inclusion of a stated integer or group of integers but not the exclusion of any other integer or group of integers.

What is claimed is:

1. A stent graft comprising a connection socket, the stent graft comprising a tubular body of a biocompatible material, the tubular body being of a selected diameter and comprising an outside surface, the connection socket comprising a first expansion restricting structure ring around the tubular body at one end thereof and a second expansion restricting structure ring spaced apart along the tubular body from the first ring, wherein the first ring comprises a first wire formed from a material selected from shape memory alloy and stainless steel and the second ring comprises a second wire formed from a material selected from shape memory alloy and stainless steel, the first ring comprising at least two turns of the first wire with each end of the first wire terminating in a loop and the second ring comprising at least two turns of the second wire with each end of the second wire terminating in a loop, the first ring and the second ring being fastened to the tubular body by stitching of the respective loops on the respective rings to the biocompatible graft material whereby to prevent the respective rings from being expanded by pressure of a self expanding or balloon expandable stent placed therein and expanded, the first ring and the second ring being of lesser diameter than the selected diameter of the tubular body, and a zigzag self contracting stent between the first ring and the second ring, the self contracting stent comprising a shape memory wire and defining a cylindrical form having a diameter less than both the selected diameter of the tubular body and the diameter of the first and second rings.

2. A stent graft as in claim 1 wherein the self contracting stent is on the outside surface of the tubular body.

3. A stent graft as in claim 1 wherein the first and second rings are on the outside surface of the tubular body.

4. A stent graft comprising a main tube of a biocompatible material and a side arm being a tube of biocompatible graft material extending from the main tube and being in fluid communication therewith, the side arm tube being of a selected diameter, the side arm comprising a connection socket at a distal end thereof, the connection socket comprising a first expansion restricting structure ring around the side arm tube at a distal end thereof and a second expansion restricting structure ring spaced apart along the side arm tube from the first ring, wherein the first ring comprises a first wire formed from a material selected from shape memory alloy and stainless steel and the second ring comprises a second wire formed from a material selected from shape memory alloy and stainless steel, the first ring comprising at least two turns of the first wire with each end of the first wire terminating in a loop and the second ring comprising at least two turns of the second wire with each end of the second wire terminating in a loop, the first ring and the second ring being fastened to the tubular body by stitching of the respective loops on the respective rings to the biocompatible graft material whereby to prevent the respective rings from being expanded by pressure of a self expanding or balloon expandable stent placed therein and expanded, the first ring and the second ring being of lesser diameter than the selected diameter of the side arm tube, and a zigzag self contracting stent between the first ring and the second ring, the self contracting stent comprising a shape memory wire and defining a cylindrical form having a diameter less than both the selected diameter of the side arm tube and the diameter of the first and second rings.

5. A bifurcated stent graft comprising a main tube of a biocompatible graft material and bifurcation defining first and second legs extending from the main tube and being in fluid communication with the main tube, each of the legs being formed from a tube of biocompatible graft material, a connection socket on at least one of the legs for a leg extension, the at least one of the legs being of a selected diameter, the connection socket comprising a first expansion restricting structure ring around the at least one of the legs at a distal end thereof and a second expansion restricting structure ring spaced apart along the at least one of the legs from the first ring, wherein the first ring comprises a first wire formed from a material selected from shape memory alloy and stainless steel and the second ring comprises a second wire formed from a material selected from shape memory alloy and stainless steel, the first ring comprising at least two turns of the first wire with each end of the first wire terminating in a loop and the second ring comprising at least two turns of the second wire with each end of the second wire terminating in a loop, the first ring and the second ring being fastened to the tubular body by stitching of the respective loops on the respective rings to the biocompatible graft material whereby to prevent the respective rings from being expanded by pressure of a self expanding or balloon expandable stent placed therein and expanded, the first ring and the second ring being of lesser diameter than the selected diameter of the at least one of the legs, and a zigzag self contracting stent between the first ring and the second ring, the self contracting stent comprising a shape memory wire and defining a cylindrical form having a diameter less than both the selected diameter of the at least one of the legs and the diameter of the first and second rings.

6. The bifurcated stent graft as in claim 5 comprising a shorter leg and a longer leg and the connection socket being on the shorter leg.

* * * * *